United States Patent
Robinson et al.

(10) Patent No.: US 10,499,946 B2
(45) Date of Patent: *Dec. 10, 2019

(54) ATHERECTOMY DEVICES AND METHODS

(71) Applicant: Cardio Flow, Inc., St. Paul, MN (US)

(72) Inventors: Paul Joseph Robinson, Mahtomedi, MN (US); Cassandra Ann Piippo Svendsen, Blaine, MN (US); Charles Anthony Plowe, Blaine, MN (US); Albert Selden Benjamin, St. Paul, MN (US)

(73) Assignee: Cardio Flow, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/150,711

(22) Filed: Oct. 3, 2018

(65) Prior Publication Data

US 2019/0029717 A1 Jan. 31, 2019

Related U.S. Application Data

(60) Continuation of application No. 16/150,003, filed on Oct. 2, 2018, which is a continuation of application
(Continued)

(51) Int. Cl.
*A61B 17/3207* (2006.01)
*A61B 17/22* (2006.01)
(Continued)

(52) U.S. Cl.
CPC .......... *A61B 17/320758* (2013.01); *A61B 2017/22038* (2013.01); *A61B 2017/22069* (2013.01);
(Continued)

(58) Field of Classification Search
CPC .......... A61B 17/32; A61B 17/32002; A61B 17/320016; A61B 17/3207; A61B 17/320758; A61B 2017/32004; A61B 2017/32008; A61B 2017/320012; A61B 2017/320708; A61B 2017/320719;
(Continued)

(56) References Cited

U.S. PATENT DOCUMENTS 1,431,416 A 10/1922 Parsons et al.
1,916,085 A 6/1933 Summers et al.
(Continued)

FOREIGN PATENT DOCUMENTS

CN 104955406 9/2015
EP 0419154 3/1991
(Continued)

OTHER PUBLICATIONS

"Declaration of Dr. Morten Olgaard Jensen," IPR2018-01658, Exhibit 1002, dated Sep. 4, 2018.
(Continued)

*Primary Examiner* — Kathleen S Holwerda
*Assistant Examiner* — Kankindi Rwego
(74) *Attorney, Agent, or Firm* — Fish & Richardson P.C.

(57) ABSTRACT

This document describes rotational atherectomy devices and systems for removing or reducing stenotic lesions in blood vessels by rotating an abrasive element within the vessel to partially or completely remove the stenotic lesion material.

31 Claims, 6 Drawing Sheets

Related U.S. Application Data

No. 16/148,347, filed on Oct. 1, 2018, which is a continuation of application No. 16/142,583, filed on Sep. 26, 2018, now Pat. No. 10,327,803, which is a continuation of application No. 15/707,690, filed on Sep. 18, 2017, now Pat. No. 10,368,901, which is a division of application No. 14/155,549, filed on Jan. 15, 2014, now Pat. No. 9,788,853.

(51) Int. Cl.
 *A61B 17/32* (2006.01)
 *A61M 25/10* (2013.01)

(52) U.S. Cl.
 CPC .............. *A61B 2017/320004* (2013.01); *A61B 2017/320766* (2013.01); *A61M 2025/1047* (2013.01); *A61M 2025/1097* (2013.01)

(58) Field of Classification Search
 CPC ....... A61B 2017/320725; A61B 2017/320733; A61B 2017/320741; A61B 2017/320766; A61B 2017/320775; A61B 2017/320783; A61B 2017/320791; A61M 25/104; A61M 25/1011; A61M 2025/1013; A61M 2025/1015; A61M 2025/1043; A61M 2025/1045; A61M 2025/1047; A61M 2025/105; A61M 2025/1084; A61M 2025/1086; A61M 2025/1095
 See application file for complete search history.

(56) References Cited

U.S. PATENT DOCUMENTS

| | | | |
|---|---|---|---|
| 4,445,509 A | 5/1984 | Auth |
| 4,445,892 A | 5/1984 | Hussein et al. |
| 4,646,736 A | 3/1987 | Auth |
| 4,784,636 A | 11/1988 | Rydell |
| 4,870,953 A | 10/1989 | DonMicheal et al. |
| 4,931,635 A | 6/1990 | Toyama |
| 4,990,134 A | 2/1991 | Auth |
| 5,100,425 A | 3/1992 | Fischell et al. |
| 5,217,474 A | 6/1993 | Zacca et al. |
| 5,242,460 A | 9/1993 | Klein et al. |
| 5,250,059 A | 10/1993 | Andreas |
| 5,250,060 A | 10/1993 | Carbo et al. |
| 5,273,526 A | 12/1993 | Dance |
| 5,308,354 A | 5/1994 | Zacca et al. |
| 5,312,427 A | 5/1994 | Shturman |
| 5,314,407 A | 5/1994 | Auth et al. |
| 5,314,438 A | 5/1994 | Shturman |
| 5,342,292 A | 8/1994 | Nita et al. |
| 5,361,285 A | 11/1994 | Formanek et al. |
| 5,370,653 A | 12/1994 | Cragg |
| 5,458,575 A | 10/1995 | Wang |
| 5,556,389 A | 9/1996 | Liprie |
| 5,584,843 A † | 12/1996 | Wulfman |
| 5,681,336 A | 10/1997 | Clement et al. |
| 5,730,717 A | 3/1998 | Gelbfish |
| 5,816,923 A | 10/1998 | Milo et al. |
| 5,836,957 A | 11/1998 | Schulz |
| 5,843,103 A | 12/1998 | Wulfman |
| 5,868,708 A | 2/1999 | Hart et al. |
| 5,897,566 A | 4/1999 | Shturman |
| 6,001,112 A | 12/1999 | Taylor |
| 6,010,533 A | 1/2000 | Pope et al. |
| 6,022,363 A | 2/2000 | Walker et al. |
| 6,066,152 A | 5/2000 | Strauss et al. |
| 6,096,054 A | 8/2000 | Wyzgala et al. |
| 6,132,444 A † | 10/2000 | Shturman |
| 6,135,982 A | 10/2000 | Campbell |
| 6,146,395 A | 11/2000 | Kanz et al. |
| 6,152,911 A | 11/2000 | Giannoble |
| 6,156,048 A | 12/2000 | Wulfman et al. |
| 6,241,706 B1 | 6/2001 | Leschinsky et al. |
| 6,270,465 B1 | 8/2001 | Keith et al. |
| 6,416,526 B1 | 7/2002 | Wyzgala et al. |
| 6,485,500 B1 | 11/2002 | Kokish et al. |
| 6,491,660 B2 | 12/2002 | Guo et al. |
| 6,494,890 B1 | 12/2002 | Shturman et al. |
| 6,565,588 B1 | 5/2003 | Clement et al. |
| 6,685,718 B1 | 2/2004 | Wyzgala et al. |
| 6,733,513 B2 | 5/2004 | Boyle |
| 6,955,661 B1 | 10/2005 | Herweck et al. |
| 8,109,954 B2 | 2/2012 | Shturman |
| 8,109,955 B2 | 2/2012 | Shturman |
| 8,137,369 B2 | 3/2012 | Shturman |
| 8,142,458 B2 | 3/2012 | Shturman |
| 8,147,507 B2 | 4/2012 | Shturman |
| 8,157,825 B2 | 4/2012 | Shturman |
| 8,177,801 B2 † | 5/2012 | Kallok |
| 8,348,965 B2 | 1/2013 | Prudnikov |
| 8,388,636 B2 | 3/2013 | Shturman |
| 8,388,637 B2 | 3/2013 | Shturman |
| 8,454,638 B2 | 6/2013 | Shturman |
| 8,465,510 B2 | 6/2013 | Shturman |
| 8,496,678 B2 | 7/2013 | Shturman |
| 8,500,764 B2 | 8/2013 | Shturman |
| 8,500,765 B2 | 8/2013 | Shturman |
| 8,628,550 B2 | 1/2014 | Narveson |
| 8,663,195 B2 | 3/2014 | Shturman |
| 8,663,260 B2 | 3/2014 | Shturman |
| 8,663,261 B2 | 3/2014 | Shturman |
| 9,289,230 B2 † | 3/2016 | Cambronne |
| 9,788,853 B2 | 1/2017 | Robinson |
| 2002/0007190 A1 | 1/2002 | Wulfman et al. |
| 2002/0082547 A1 | 6/2002 | Deniega et al. |
| 2002/0099367 A1 | 7/2002 | Guo et al. |
| 2002/0138088 A1 | 9/2002 | Nash et al. |
| 2002/0188276 A1 | 12/2002 | Evans et al. |
| 2003/0199889 A1 | 10/2003 | Kanz et al. |
| 2004/0098014 A1 | 5/2004 | Flugelman et al. |
| 2004/0158270 A1 | 8/2004 | Wyzgala et al. |
| 2005/0154416 A1 | 7/2005 | Herweck et al. |
| 2005/0209615 A1 | 9/2005 | Prudnikov et al. |
| 2005/0240146 A1 | 10/2005 | Nash et al. |
| 2005/0256461 A1 | 11/2005 | DiFiore et al. |
| 2007/0006688 A1 | 1/2007 | Shyu |
| 2008/0097498 A1 | 4/2008 | Shimizu et al. |
| 2008/0306498 A1 | 12/2008 | Thatcher |
| 2008/0319415 A1 | 12/2008 | Shturman |
| 2009/0018564 A1 | 1/2009 | Shturman |
| 2009/0069829 A1 † | 3/2009 | Shturman |
| 2009/0105736 A1 | 4/2009 | Prudnikov |
| 2009/0182359 A1 | 7/2009 | Shturman |
| 2009/0264908 A1 | 10/2009 | Kallok |
| 2009/0312777 A1 | 12/2009 | Shturman |
| 2009/0318942 A1 | 12/2009 | Shturman |
| 2009/0326568 A1 | 12/2009 | Shturman |
| 2010/0010522 A1 | 1/2010 | Shturman |
| 2010/0049226 A1 | 2/2010 | Shturman |
| 2010/0211088 A1 † | 8/2010 | Narveson |
| 2011/0009888 A1 | 1/2011 | Shturman |
| 2011/0054332 A1 | 3/2011 | Shturman |
| 2012/0178986 A1 | 1/2012 | Campbell et al. |
| 2012/0035633 A1 † | 2/2012 | Shturman |
| 2012/0109170 A1 | 5/2012 | Shturman |
| 2012/0150207 A1 | 6/2012 | Shturman |
| 2012/0191113 A1 | 7/2012 | Shturman |
| 2013/0103062 A1 † | 4/2013 | To |
| 2013/0178881 A1 | 7/2013 | Shturman |
| 2013/0245654 A1 | 9/2013 | Shturman |
| 2013/0274773 A1 | 10/2013 | Shturman |
| 2013/0296904 A1 | 11/2013 | Shturman |
| 2013/0296905 A1 | 11/2013 | Shturman |
| 2013/0310589 A1 | 11/2013 | Shturman |
| 2014/0081298 A1 | 3/2014 | Cambronne |
| 2015/0080795 A1 | 3/2015 | Mattison et al. |

FOREIGN PATENT DOCUMENTS

| | | |
|---|---|---|
| EP | 0 820 729 | 1/1998 |
| EP | 1 820 458 | 8/2007 |

(56) References Cited

FOREIGN PATENT DOCUMENTS

| GB | 2426458 | 5/2005 |
|---|---|---|
| WO | WO 1998/50101 | 11/1998 |
| WO | WO 1999/44513 | 9/1999 |
| WO | WO 2001/15759 | 3/2001 |
| WO | WO 2002/09599 | 2/2002 |
| WO | WO 2006/126076 | 11/2006 |
| WO | WO 2006/126175 | 11/2006 |
| WO | WO 2006/126176 | 11/2006 |
| WO | WO 2010/112618 | 10/2010 |
| WO | WO 2014/042752 | 3/2014 |

OTHER PUBLICATIONS

"Declaration of Kristina Rouw, PhD," IPR2018-01658, Exhibit 2001, dated Dec. 10, 2018.

"Petition for Inter Partes Review of U.S. Pat. No. 9,089,362 Under 35 U.S.C. § 312 and 37 C.F.R. § 42.104," *Cardiovascular Systems, Inc.* v. *Cardio Flow, Inc.*, IPR2018-01658, Paper 1, dated Sep. 5, 2018.

"Patent Owner's Preliminary Response," IPR2018-01658, Paper 6, dated Dec. 11, 2018.

Declaration of Aleksey Filippov, Apr. 23, 2007, 1 page.

Declaration of Dmitri Prudnikov, Apr. 23, 2007, 1 page.

Excerpt from Deposition of Dmitri Prudnikov, Mar. 5, 2008, 7 pages.

Excerpt from Deposition of Dmitri Prudnikov, Mar. 6, 2008, 54 pages.

Exhibits Nos. 14, 31 & 32, from Deposition of Dmitri Prudnikov, Mar. 5, 2008, 3 pages.

Exhibits Nos. 33-39 from Deposition of Dmitri Prudnikov, Mar. 6, 2008, 47 pages.

European Search Report in Application No. 15737946.2, dated Aug. 1, 2017, 8 pages.

EP Office Action in European Appln. No. 15737946.2, dated Jul. 12, 2018.

"Declaration of Dr. Morten Olgaard Jensen," IPR2018-01549, Exhibit 1002, dated Aug. 15, 2018, 103 pages.

"Declaration of Kristina Rouw, Ph.D," IPR2018-01549, Exhibit 2001, dated Nov. 29, 2018, 45 pages.

"Patent Owner's Preliminary Response," IPR2018-01549, Paper 8, dated Nov. 29, 2018.

"Petition for Inter Partes Review of U.S. Pat. No. 9,788,853 Under 35 U.S.C. § 312 and 37 C.F.R. § 42.104," *Cardiovascular Systems, Inc.* Petitioner v. *Cardio Flow, Inc.* Patent Owner, IPR2018-01549, Paper 1, dated Aug. 17, 2018.

† cited by third party

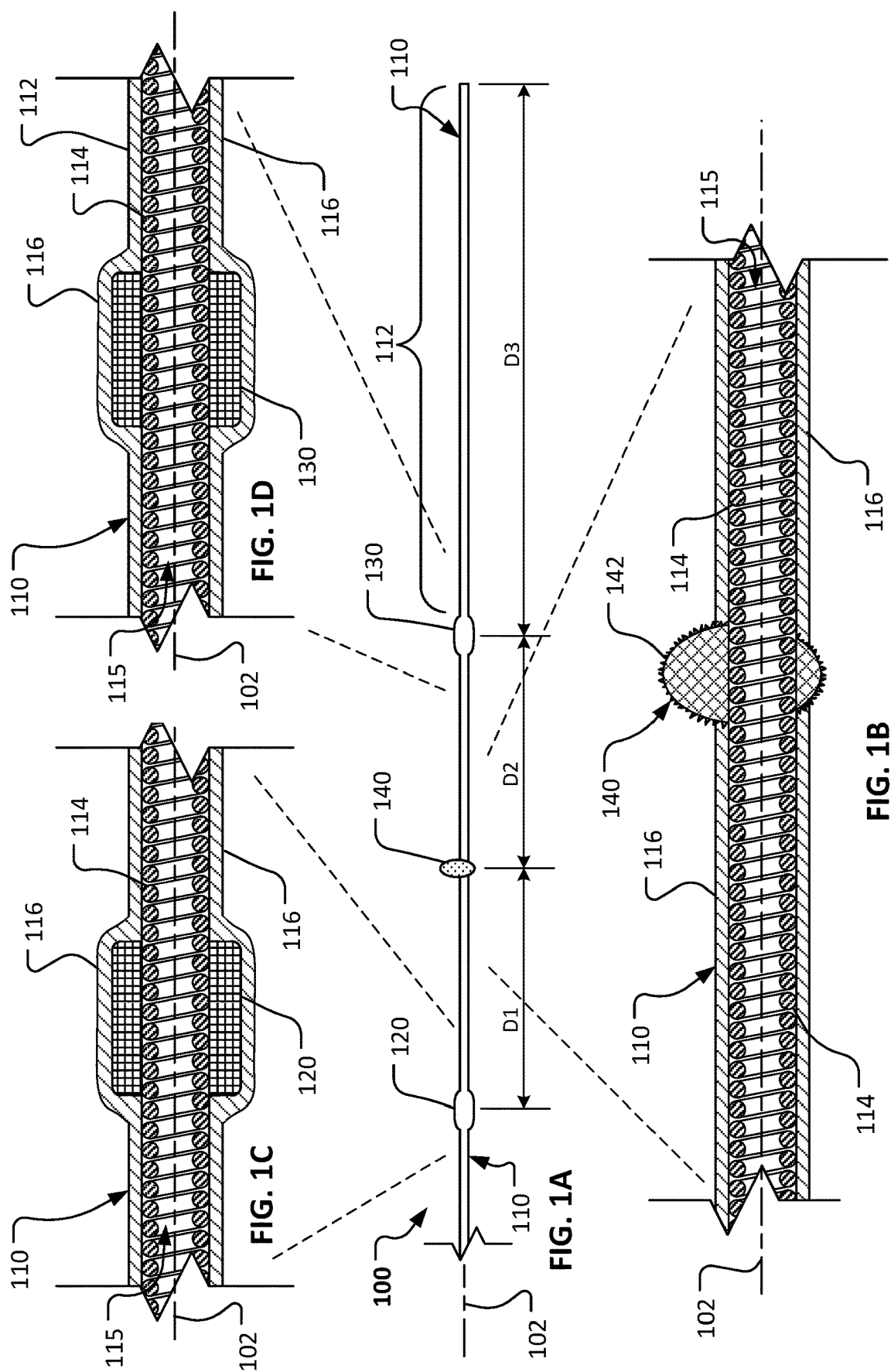

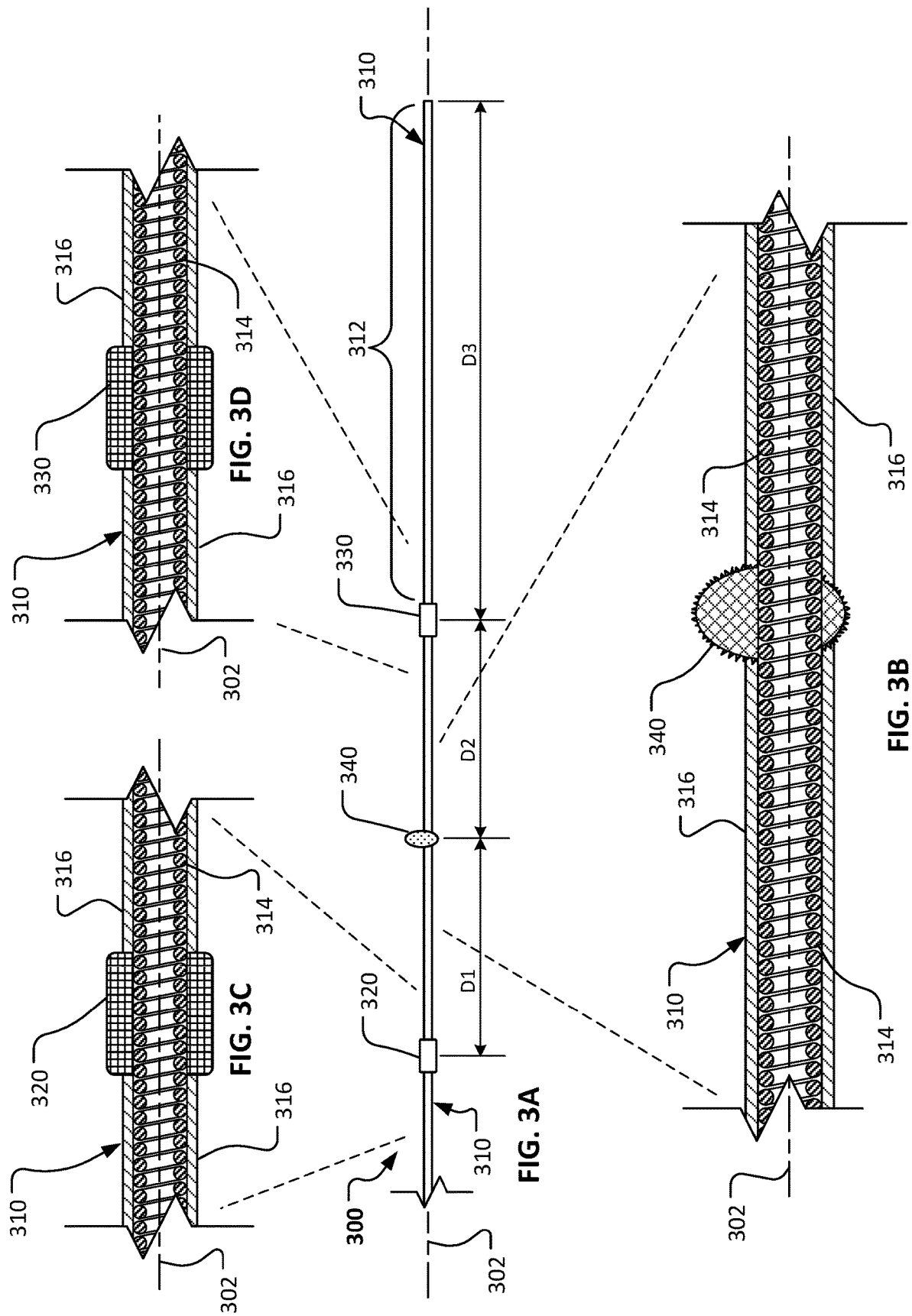

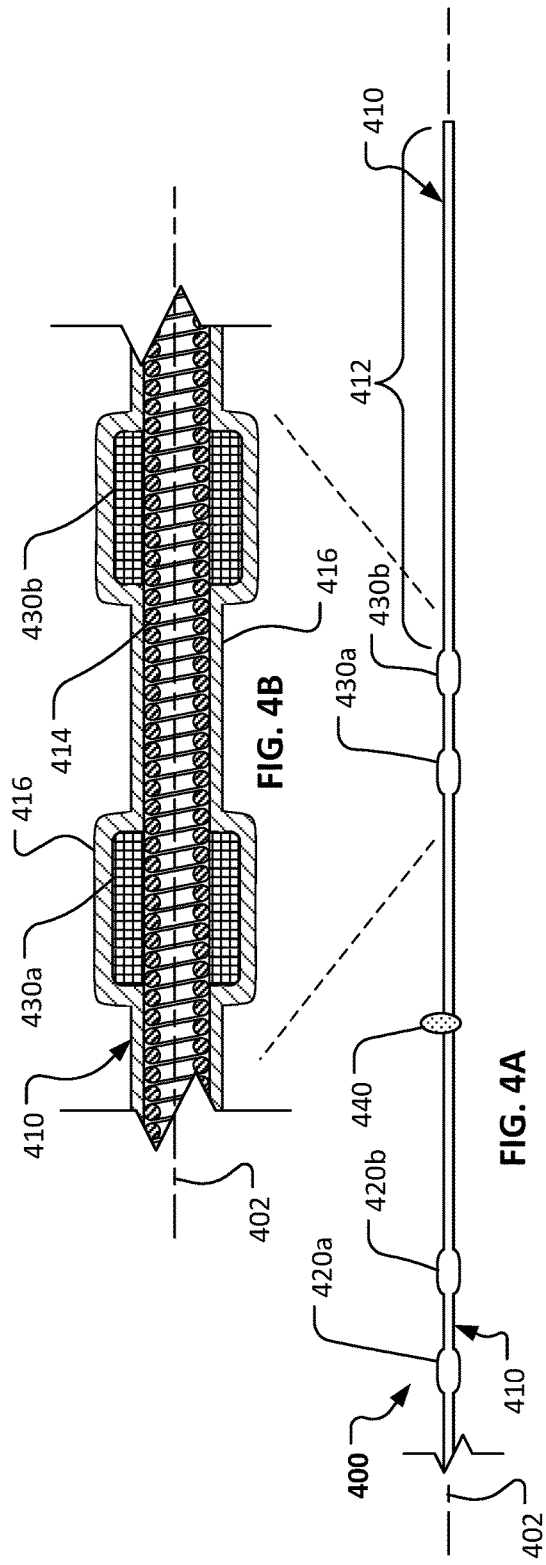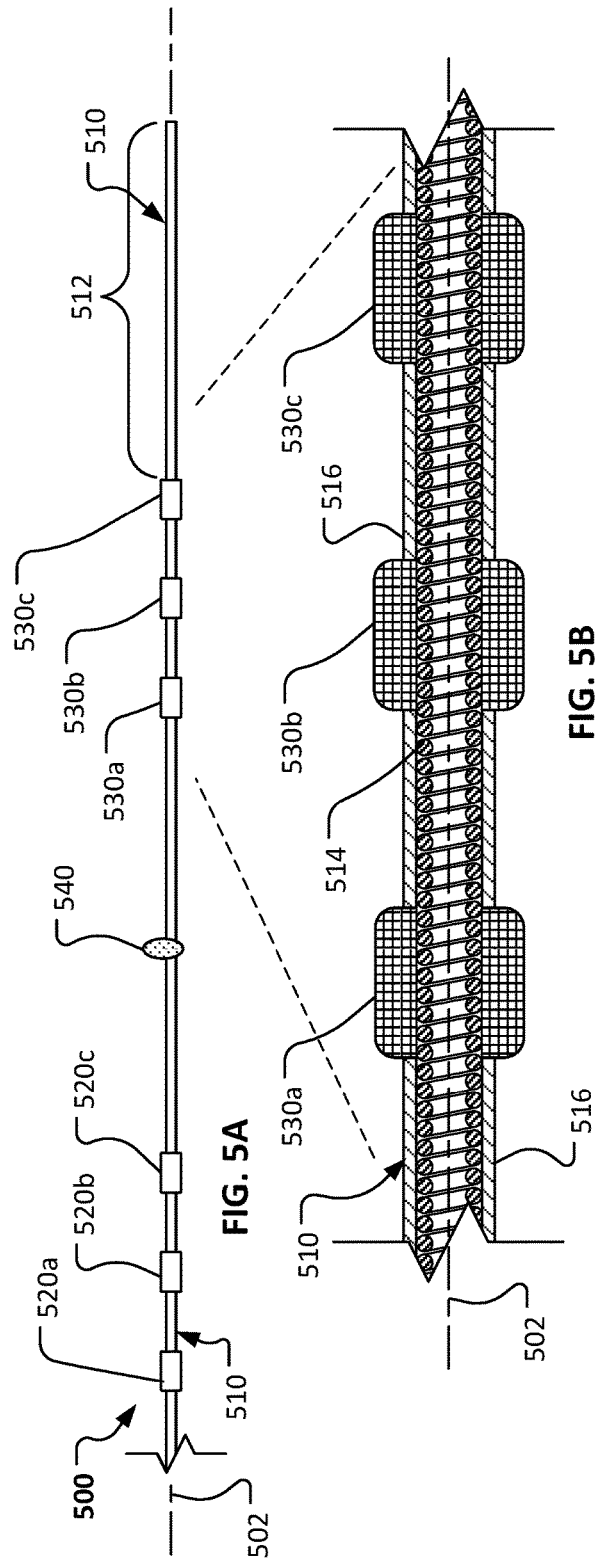

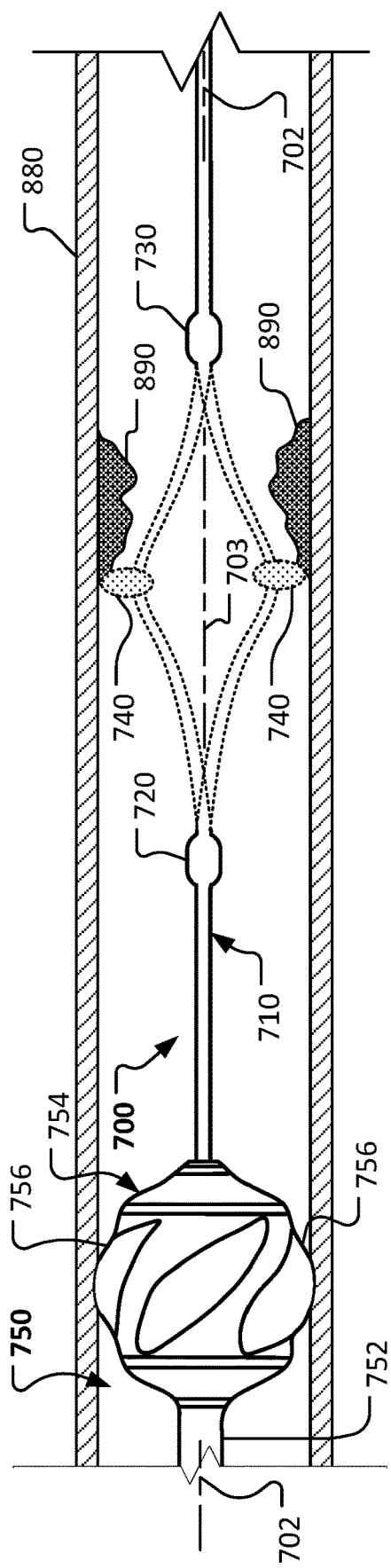
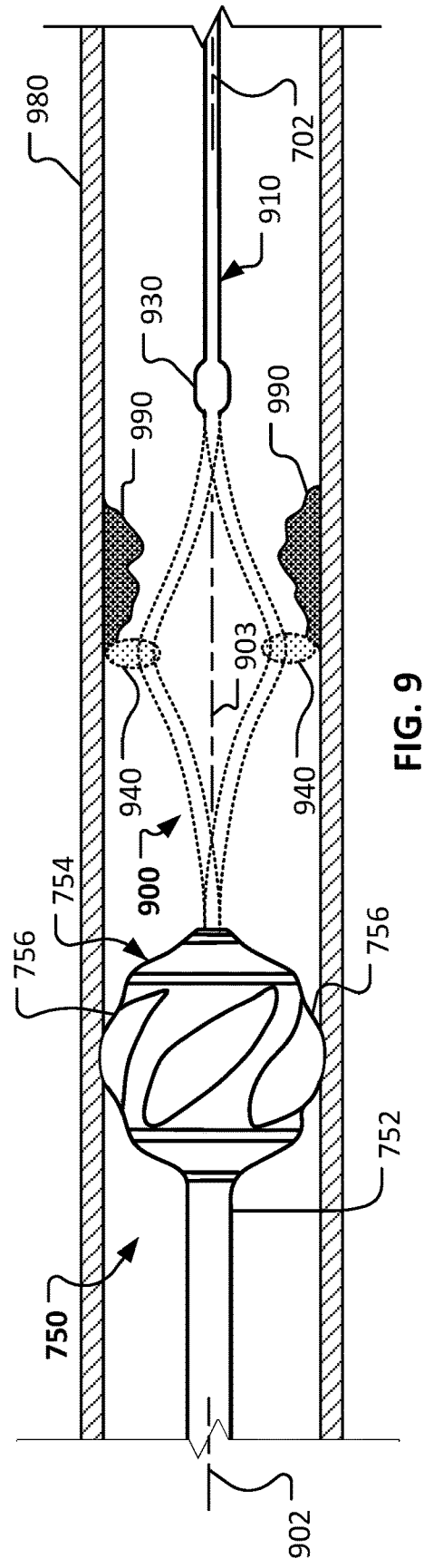
FIG. 8
FIG. 9

US 10,499,946 B2

ATHERECTOMY DEVICES AND METHODS

CLAIM OF PRIORITY

This application is a continuation of U.S. patent application Ser. No. 16/150,003 filed on Oct. 2, 2018, which is a continuation of U.S. patent application Ser. No. 16/148,347 filed on Oct. 1, 2018, which is a continuation of U.S. patent application Ser. No. 16/142,583 filed on Sep. 26, 2018, which is a continuation of U.S. patent application Ser. No. 15/707,690 filed on Sep. 18, 2017, which is a divisional application and claims priority to U.S. patent application Ser. No. 14/155,549, filed on Jan. 15, 2014, the entire contents of which are hereby incorporated by reference.

TECHNICAL FIELD

This document relates to rotational atherectomy devices and systems for removing or reducing stenotic lesions in blood vessels, for example, by rotating an abrasive element within the vessel to partially or completely remove the stenotic lesion material.

BACKGROUND

Atherosclerosis, the clogging of arteries with plaque, is often a cause of coronary heart disease or vascular problems in other regions of the body. Plaque is made up of fat, cholesterol, calcium, and other substances found in the blood. Over time, the plaque hardens and narrows the arteries. This limits the flow of oxygen-rich blood to organs and other parts of the body.

Blood flow through the peripheral arteries (e.g., carotid, iliac, femoral, renal etc.), can be similarly affected by the development of atherosclerotic blockages. Peripheral artery disease (PAD) can be serious because without adequate blood flow, the kidneys, legs, arms, and feet may suffer irreversible damage. Left untreated, the tissue can die or harbor infection.

One method of removing or reducing such blockages in blood vessels is known as rotational atherectomy. In some implementations, a drive shaft carrying an abrasive burr or other abrasive surface (e.g., formed from diamond grit or diamond particles) rotates at a high speed within the vessel, and the clinician operator slowly advances the atherectomy device distally so that the abrasive burr scrapes against the occluding lesion and disintegrates it, reducing the occlusion and improving the blood flow through the vessel. Examples of some rotational atherectomy devices are depicted in U.S. Patent Publication Nos. 2009/0018564, 2009/0182359, 2009/0069829, 2009/0312777, 2009/0326568, 2009/0318942, 2010/0010522, 2010/0049226, 2011/0009888, 2012/0109170, and 2012/0035633; British Patent Publication No. GB2454943; and U.S. Pat. Nos. 4,990,134; 5,314,438; 6,132,444 and 6,146,395.

SUMMARY

Some embodiments of rotational atherectomy devices and systems described herein can remove or reduce stenotic lesions in blood vessels by rotating an abrasive element according to a stable and predictable orbiting profile. In particular embodiments, a rotational atherectomy device comprises an elongate flexible drive shaft with an eccentric abrasive element that is attached to the drive shaft, and two or more weighted stability elements are attached to the drive shaft such that at least one stability element is on each side of the abrasive element. Optionally, the stability elements have a center of mass that is axially aligned with a central longitudinal axis of the drive shaft while the eccentric abrasive element has a center of mass that is axially offset from central longitudinal axis of the drive shaft. A flexible polymer coating may surround at least a portion of the drive shaft, including the stability elements in some embodiments. Also, in some optional embodiments, a distal extension portion of the drive shaft may extend distally beyond the distal-most stability element.

In one aspect, this document provides a rotational atherectomy device for removing stenotic lesion material from a blood vessel of a patient. In some embodiments, the rotational atherectomy device includes an elongate flexible drive shaft comprising a torque-transmitting coil that defines a longitudinal axis, and the drive shaft is configured to rotate about the longitudinal axis. The rotational atherectomy device may also include an abrasive element that is attached to the drive shaft such that a center of mass of the abrasive element is offset from the longitudinal axis of the drive shaft. The rotational atherectomy device may also include a proximal stability element that is fixed to the drive shaft and that has a center of mass aligned with the longitudinal axis of the drive shaft. The proximal stability element can be proximally spaced apart from the abrasive element. The rotational atherectomy device may also include a distal stability element that is fixed to the drive shaft and that has a center of mass aligned with the longitudinal axis of the drive shaft. The distal stability element can be distally spaced apart from the abrasive element. The rotational atherectomy device may also include a flexible polymer coating along the drive shaft, such that the coating surrounds an outer diameter of at least a portion of drive shaft.

In various implementations of the rotational atherectomy device, the proximal and distal stability elements may be equally spaced apart from the abrasive element by a stability spacing distance. The drive shaft may optionally comprise a distal-most extension portion that extends distally of the distal stability element for a distal extension distance. The distal extension distance may be substantially greater than the stability spacing distance. In some embodiments, the drive shaft may have a central lumen extending along the longitudinal axis that is configured to receive a guidewire. The proximal and distal stability elements may comprise hollow cylinders that surround the torque-transmitting coil of the drive shaft. In particular embodiments, the hollow cylinders may have an exterior cylindrical surface that is smoother and different from an abrasive exterior surface of the abrasive element. Optionally, the hollow cylinders may have an axial length that is greater than a maximum exterior diameter of the hollow cylinders. The flexible polymer coating surrounds the torque-transmitting coil of the drive shaft extending between the first and second stability elements, and exteriors of the abrasive element and the proximal and distal stability elements are uncoated and outwardly exposed.

In some embodiments of the rotational atherectomy device, the flexible polymer coating may surround the torque-transmitting coil of the drive shaft extending between the first and second stability elements. In some such embodiments, the exteriors of the abrasive element and the proximal and distal stability elements may be uncoated and outwardly exposed. In particular embodiments, the flexible polymer coating may surround the outer diameter of the drive shaft extending between the first and second stability elements and may surround exterior surfaces of the first and second stability elements. In some such embodiments, an abrasive outer surface of the abrasive element may be uncoated and outwardly exposed. Optionally, the flexible polymer coating may comprise a fluid-impermeable material that provides a fluid-impermeable lumen along the drive shaft. In some embodiments, the flexible polymer coating may have a different durometer at different locations on the drive shaft.

In some implementations, the rotational atherectomy device may further comprise a second proximal stability element and a second distal stability element. Optionally, the second proximal stability element may be located proximally to the abrasive element and the second distal stability element may be located distally to the abrasive element. In some embodiments, the abrasive element may comprise two or more abrasive segments that may be positioned adjacent to one another along the drive shaft. In particular embodiments, the abrasive element may comprise at least three segments, and a middle segment may optionally have a larger outer diameter than a proximal segment and a larger outer diameter than a distal segment.

In another aspect, this document provides a system for performing rotational atherectomy to remove stenotic lesion material from a blood vessel of a patient. In some embodiments, the system includes an elongate flush tube defining a first lumen and a second lumen. The flush tube may include an inflatable balloon member attached to and surrounding an outer diameter of a distal end portion of the flush tube. The balloon member can be in fluid communication with the first lumen. The balloon member can be configured to contact a blood vessel wall when the balloon member is in an inflated configuration. The system also includes a rotational atherectomy device. The rotational atherectomy device can include an elongate flexible drive shaft defining a longitudinal axis. The drive shaft can be configured for rotation about the longitudinal axis and configured to be at least partially disposed within the second lumen when the system is used for performing the rotational atherectomy. The rotational atherectomy device can also include an abrasive element that is fixed to the drive shaft such that a center of mass of the abrasive element is offset from the longitudinal axis. The rotational atherectomy device can also include a stability element that is fixed to the drive shaft and that has a center of mass aligned with the longitudinal axis, the second stability element being distally spaced apart from the abrasive element.

In various implementations of the system for performing rotational atherectomy, the balloon member may optionally define channel spaces that are configured to allow blood flow therethrough when the balloon member is in the inflated configuration within the blood vessel. In some embodiments, the system for performing rotational atherectomy can further comprise a second stability element that may be fixed to the drive shaft and located proximally of the abrasive element. The system may further comprise a guidewire that can be configured to slidably withdrawn into a fluid-impermeable lumen of the drive shaft of rotational atherectomy device. In some embodiments of the system for performing rotational atherectomy, the rotational atherectomy device may further comprise a flexible polymer coating along the drive shaft such that the coating may surround an outer diameter of at least a portion of drive shaft.

In another aspect, this document provides a method for performing rotational atherectomy to remove stenotic lesion material from a blood vessel of a patient. In some embodiments, the method includes delivering a rotational atherectomy device into the blood vessel. In some embodiments, the rotational atherectomy device includes an elongate flexible drive shaft defining a longitudinal axis. The drive shaft can be configured for rotation about the longitudinal axis. The rotational atherectomy device can also include an abrasive element that is fixed to the drive shaft such that a center of mass of the abrasive element is offset from the longitudinal axis. The rotational atherectomy device can also include a first stability element that is fixed to the drive shaft and that has a center of mass aligned with the longitudinal axis. The first stability element can be proximally spaced apart from the abrasive element. The rotational atherectomy device can also include a second stability element that is fixed to the drive shaft and that has a center of mass aligned with the longitudinal axis. The second stability element can be distally spaced apart from the abrasive element. The method for performing rotational atherectomy to remove stenotic lesion material from a blood vessel of a patient can also include rotating the drive shaft about the longitudinal axis such that a portion of the drive shaft extending between the first and second stability elements traces a generally bicone shape.

In various implementations of the method for performing rotational atherectomy to remove stenotic lesion material from a blood vessel of a patient, during the rotation, the abrasive element may have an orbital path about an axis of rotation. The orbital path may have a substantially greater diameter than a travel path of each of the first and second stability elements. In some embodiments, the method for performing rotational atherectomy may further comprise translating the drive shaft distally during the rotating the drive shaft. The rotating the drive shaft may cause the abrasive element to remove the stenotic lesion material from a vessel wall. In some embodiments, the method for performing rotational atherectomy may further comprise delivering an elongate flush tube into the blood vessel. The flush tube may define a first lumen and a second lumen. The flush tube may include a balloon member attached to and surrounding an outer diameter of a distal end portion of the flush tube. The balloon member may be in fluid communication with the first lumen, and at least a portion of the drive shaft may be disposed within the second lumen. Optionally, the method for performing rotational atherectomy may further comprise inflating the balloon member by supplying an inflation fluid through the first lumen. The inflating may cause the balloon member to expand into contact with the blood vessel.

Some of the embodiments described herein may provide one or more of the following advantages. First, some embodiments of the rotational atherectomy devices and systems operate with a stable and predictable rotary motion profile for enhanced atherectomy performance. That is, when the device is being rotated in operation, the eccentric abrasive element follows a predefined, consistent orbital path (offset from an axis of rotation of the device) while the stability elements and other portions of the device remain on or near to the axis of rotation for the drive shaft in a stable manner. This predictable orbital motion profile can be attained by the use of design features including, but not limited to, stability elements that have centers of mass that are coaxial with the longitudinal axis of the drive shaft, a polymeric coating on at least a portion of the drive shaft, a distal-most drive shaft extension portion, and the like. Some embodiments of the rotational atherectomy devices and systems provided herein may include one or more of such design features.

Second, some embodiments of the rotational atherectomy devices and systems provided herein can be used to treat large-diameter vessels (including renal and iliac arteries having an internal diameter that is multiple time greater than the outer diameter of the abrasive element) while requiring only a small introducer sheath size. In other words, in some embodiments the rotating eccentric abrasive element traces an orbital path that is substantially larger than the outer diameter of the rotational atherectomy device in the non-rotating state. This feature improves the ability of the rotational atherectomy devices provided herein to treat very large vessels while still fitting within a small introducer size. In some embodiments, this feature can be at least partially attained when a guidewire that is used to navigate the atherectomy device to the site of the target lesion is withdrawn prior to rotation of the drive shaft, such that the guidewire does not resist the deflection of the drive shaft during rotation. Further, in some embodiments this feature can be at least partially attained by using an eccentric abrasive element that has a high eccentric mass (e.g., the center of mass of the abrasive element is significantly offset from the central longitudinal axis of the drive shaft).

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a side view of a distal portion of a rotational atherectomy device, in accordance with some embodiments.

FIG. 1B is a longitudinal cross-sectional view of a portion of the rotational atherectomy device of FIG. 1A, including the device's eccentric abrasive element.

FIGS. 1C and 1D are longitudinal cross-sectional views of portions of the rotational atherectomy device of FIG. 1A that include the device's stability elements.

FIG. 3A is a side view of a distal portion of another rotational atherectomy device, in accordance with some embodiments.

FIG. 3B is a longitudinal cross-sectional view of a portion of the rotational atherectomy device of FIG. 3A, including the device's eccentric abrasive element.

FIGS. 3C and 3D are longitudinal cross-sectional views of portions of the rotational atherectomy device of FIG. 3A that include the device's stability elements.

FIG. 4A is a side view of a distal portion of another rotational atherectomy device, in accordance with some embodiments.

FIG. 4B is a longitudinal cross-sectional view of a portion of the rotational atherectomy device of FIG. 4A, including some of the device's stability elements.

FIG. 5A is a side view of a distal portion of another rotational atherectomy device, in accordance with some embodiments.

FIG. 5B is a longitudinal cross-sectional view of a portion of the rotational atherectomy device of FIG. 5A, including some of the device's stability elements.

FIG. 8 is a side view of the rotational atherectomy system of FIG. 7 deployed within a vessel that is shown in longitudinal cross-section.

FIG. 9 is a side view of another rotational atherectomy system, in accordance with some embodiments, deployed within a vessel that is shown in longitudinal cross-section. Like reference symbols in the various drawings indicate like elements.

DETAILED DESCRIPTION OF ILLUSTRATIVE EMBODIMENTS

Figure 2A:
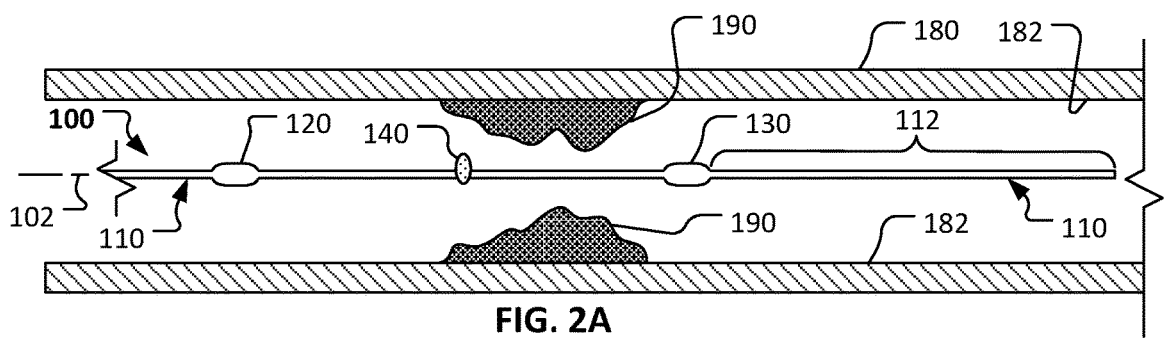
FIG. 2A is a side view of the rotational atherectomy device of FIG. 1A after being deployed within a vessel that is shown in longitudinal cross-section.

Referring to FIG. 1A, in some embodiments a rotational atherectomy device 100 can include a drive shaft 110, a proximal stability element 120, a distal stability element 130, and an eccentric abrasive element 140. In this embodiment, the stability elements 120 and 130 have a center of mass that is axially aligned with a central longitudinal axis 102 of the drive shaft 110 while the eccentric abrasive element 140 has a center of mass that is axially offset from central longitudinal axis 102 of the drive shaft 110. As will be described further below, the rotational atherectomy device 100 is configured to remove some or all of a stenotic lesion from within a vessel of a patient. As the rotational atherectomy device 100 is rotated about its longitudinal axis 102, centrifugal force will cause the eccentric abrasive element 140 to follow a transverse circular orbit around the longitudinal axis. The orbiting eccentric abrasive element 140 will contact the stenotic lesion to ablate the lesion to a reduced size.

The proximal stability element 120 and the distal stability element 130 are each fixedly attached to the drive shaft 110. The proximal stability element 120 is located proximal to the distal stability element 130. The eccentric abrasive element 140 is located between the proximal stability element 120 and the distal stability element 130. The eccentric abrasive element 140 is also fixedly attached to the drive shaft 110. A distal drive shaft extension portion 112 of the drive shaft 110 extends distally of the distal stability element 130.

Referring now to FIGS. 1A-1D, the elongate drive shaft 110 of rotational atherectomy device 100 is laterally flexible so that the drive shaft 110 can readily conform to the tortuous non-linear vasculature of the patient, and so that a portion of the drive shaft 110 adjacent to the eccentric abrasive element 140 will laterally deflect when acted on by the centrifugal forces resulting from the rotation of the eccentric abrasive element 120. In this embodiment, the drive shaft 110 comprises one or more helically wound wires 114 (or filars 114). In some embodiments, the one or more helically wound wires 114 are made of a metallic material such as, but not limited to, stainless steel (e.g., 316, 316L, or 316LVM), nitinol, titanium, titanium alloys (e.g., titanium beta 3), carbon steel, or another suitable metal or metal alloy. In some alternative embodiments, the filars 114 are or include graphite, Kevlar, or a polymeric material. In some embodiments, the filars 114 can be woven, rather than wound. In some embodiments, individual filars 114 can comprise multiple strands of material that are twisted, woven, or otherwise coupled together to form a filar 114. In some embodiments, the filars 114 have different cross-sectional geometries (size or shape) at different portions along the axial length of the drive shaft 110. In some embodiments, the filars 114 have a cross-sectional geometry other than a circle, e.g., an ovular, square, triangular, or another suitable shape. The one or more helically wound wires 114 can transmit a torque from a rotary actuator (comprising, for example, a pneumatic motor or an electric motor) located exterior to the patient (not shown in FIG. 1A). The torque from the external actuator is transmitted via the drive shaft 110 to the elements 120, 130, 140, and 112 along the distal portion of the rotational atherectomy device 100.

In this embodiment, the drive shaft 110 has a hollow core. That is, the drive shaft 110 has a longitudinal lumen 115 running therethrough. The lumen 115 can be used to receive a guidewire therein, as will be described further below. In some embodiments, the lumen can be used to aspirate particulate or to convey fluids that are beneficial for the atherectomy procedure.

The size of the drive shaft 110 can be scaled commensurately with the size of vessels to be treated and the performance desired. In a first example embodiment, the outer diameter of the drive shaft 110 is about 0.030 inches (0.76 mm) and the inner diameter is about 0.020 inches (0.51 mm). The first example embodiment uses a six (6) filar configuration with each filar having a diameter of about 0.005 inches (0.13 mm). In a second example embodiment, the outer diameter of the drive shaft 110 is about 0.051 inches (1.30 mm) and the inner diameter is about 0.041 inches (1.04 mm). The second example embodiment uses a nine (9) filar configuration with each filar having a diameter of about 0.005 inches (0.13 mm).

From the description provided herein, it should be understood that a range of sizes of drive shafts 110 are contemplated. For example, the outer diameter of the drive shaft 110 may range from about 0.020 inches to about 0.100 inches (0.50 mm to 2.54 mm). The drive shafts 110 can have any number of filars, and the diameter of the filars may range from about 0.002 inches to about 0.020 inches (0.05 mm to 0.51 mm).

In the depicted embodiment, the drive shaft 110 also includes a coating 116 on the outer diameter of the drive shaft 110. The coating 116 may also be described as a jacket, a sleeve, a covering, a casing, and the like. In some embodiments, the coating 116 adds column strength to the drive shaft 110 to facilitate a greater ability to push the drive shaft 110 through stenotic lesions. In addition, the coating 116 can enhance the stability of the drive shaft 110 during use. In some embodiments, the coating 116 is a flexible polymer coating that surrounds an outer diameter of at least a portion of drive shaft 110 (e.g., the portion of the drive shaft located exterior to the patient and extending fully to at least the proximal stability element 120). In particular embodiments, the coating 116 is a fluid impermeable material such that the lumen 115 provides a fluid impermeable flow path to the distal portion of the device 100.

The coating 116 may be made of materials including, but not limited to, PEBEX, PICOFLEX, TECOFLEX, PTFE, ePTFE, FEP, PEEK, silicone, PVC, urethane, polyethylene, polypropylene, and the like, and combinations thereof. In some embodiments, a second coating that is analogous to the coating 116 may also be included on the inner diameter of the drive shaft 110. Alternatively, the coating on the inner diameter of the drive shaft 110 may be included as an alternative to the coating 116 on the outer diameter of the drive shaft 110. In the depicted embodiment, the coating 116 covers not only the drive shaft 110, but also the proximal stability element 120, the distal stability element 130, and the distal extension portion 112, thereby leaving only the abrasive element 140 exposed (non-coated) along the distal portion of the device 100. In alternative embodiments, the proximal stability element 120 and the distal stability element 130 are not covered with the coating 116, and thus would be exposed like the abrasive element 140. In some embodiments, two or more layers of the coating 116 can be included on portions of the drive shaft 110. Further, in some embodiments different coating materials (e.g., with different durometers and/or stiffnesses) can be used at different locations on the drive shaft 110. For example, a first portion of the coating 116 extending along the drive shaft that is proximal to the proximal stability element 120 and distal to the distal stability element 130 can have a first durometer that is different from (e.g., substantially higher than) a second durometer of a second portion of the coating 116 extending between the proximal stability element 120 and the distal stability element 130.

Still referring to FIGS. 1A-1D, in this embodiment, the proximal stability element 120 and the distal stability element 130 are each hollow cylindrical members having an inner diameter that surrounds a portion of the outer diameter of the drive shaft 110. In some embodiments, the proximal stability element 120 and the distal stability element 130 have an axial length that is greater than a maximum exterior diameter of the proximal stability element 120 and the distal stability element 130. As shown in FIGS. 1C-1D, the proximal stability element 120 and the distal stability element 130 are coaxial with the longitudinal axis 102 of the drive shaft 110. Therefore, the centers of mass of the proximal stability element 120 and the distal stability element 130 are axially aligned (non-eccentric) with the longitudinal axis 102. In alternative rotational atherectomy device embodiments, stability elements that have centers of mass that are eccentric in relation to the longitudinal axis 102 may be included in addition to, or as an alternative to, the coaxial proximal and distal stability elements 120 and 130. For example, in some alternative embodiments, the stability elements can have centers of mass that are eccentric in relation to the longitudinal axis 102 and that are offset 180 degrees in relation to the center of mass of the eccentric abrasive element 140.

The proximal stability element 120 and the distal stability element 130 may be made of a suitable biocompatible material, such as a higher-density biocompatible material. For example, in some embodiments the proximal stability element 120 and the distal stability element 130 may be made of metallic materials such as stainless steel, tungsten, molybdenum, iridium, cobalt, cadmium, and the like, and alloys thereof. The proximal stability element 120 and the distal stability element 130 may be mounted to the filars 114 using a biocompatible adhesive, by welding, by press fitting, and the like, and by combinations thereof. The coating 116 may also be used to attach or to supplement the attachment of the proximal stability element 120 and the distal stability element 130 to the filars 114 of the drive shaft 110. Alternatively, the proximal stability element 120 and the distal stability element 130 can be integrally formed as a unitary structure with the filars 114 of the drive shaft 110 (e.g., using filars of a different size or density, using filars that are double-wound to provide multiple filar layers, or the like). The proximal stability element 120 and the distal stability element 130 have an exterior cylindrical surface that is smoother and different from an abrasive exterior surface of the abrasive element 140.

Still referring to FIGS. 1A-1D, the eccentric abrasive element 140, which may also be referred to as a burr, can comprise a biocompatible material that is coated with an abrasive media such as diamond grit, diamond particles, silicon carbide, and the like. As shown in FIG. 1B, the center of mass of the eccentric abrasive element 140 is offset from the longitudinal axis 102 of the rotational atherectomy device 100. The eccentric abrasive element 140 has at least one outwardly exposed surface (the abrasive surface 142) that is not covered by the coating 116. Therefore, as the eccentric abrasive element 140 is rotated in an orbital path, at least a portion of the abrasive surface 142 of the eccentric abrasive element 140 can make contact with surrounding stenotic lesion material. As with the stability elements 120 and 130, the eccentric abrasive element 140 may be mounted to the filars 114 using a biocompatible adhesive, welding, press fitting, and the like. Alternatively, the eccentric abrasive element 140 can be integrally formed as a unitary structure with the filars 114 of the drive shaft 110 (e.g., using filars that are wound in a different pattern to create an axially offset structure, or the like).

Referring again to FIG. 1A, in some embodiments, the spacing of the proximal stability element 120 and the distal stability element 130 (relative to the eccentric abrasive element 140) and the length of the distal extension portion 112 can be selected to advantageously provide a stable and predictable rotary motion profile during high-speed rotation of the device 100. For example, in this embodiment, the eccentric abrasive element 140 is separated from the proximal stability element 120 by a distance D1. The eccentric abrasive element 140 is separated from the distal stability element 130 by a distance D2. In the depicted embodiment, the distances D1 and D2 are equal. The distal driveshaft extension portion 112 is a portion of the driveshaft 110 that extends distally from the distal stability element 130 by a distance D3. In use, the distal driveshaft extension portion 112 adds to the stability of the rotational atherectomy device 100, while the eccentric abrasive element 140 is following its orbital path around the longitudinal axis 102. In the depicted embodiment, the distal driveshaft extension portion 112 is covered with the coating 116. In this particular embodiment, the distance D3 is significantly greater than the distance D1 or D2.

In embodiments that include the distal driveshaft extension portion 112, the ratio of the distance D3 to the distance D1 (or D2) can be selected to affect the performance characteristics (e.g., the stability of the rotary motion profile) of the rotational atherectomy device 100. In some embodiments, the ratio of D3:D1 (or D3:D2) is about 1:1, about 1.5:1, about 2:1, about 2.5:1, about 3:1, or higher than 3:1 It should be understood from the description herein, that in some alternative embodiments, the distances D1 and D2 may be unequal.

Referring now to FIG. 2A, the rotational atherectomy device 100 can be used to treat a vessel 180 having a stenotic lesion 190 along an inner wall 182 of the vessel 180. The rotational atherectomy device 100 is used to fully or partially remove the stenotic lesion 190, thereby removing or reducing the blockage within the vessel 180 caused by the stenotic lesion 190. By performing such a treatment, the blood flow through the vessel 180 may be thereafter increased or otherwise improved. The vessel 180 and lesion 190 are shown in longitudinal cross-sectional views to enable visualization of the rotational atherectomy device 100.

Briefly, in some implementations the following activities may occur to provide the deployed arrangement shown in FIG. 2A. An introducer sheath (not shown in FIG. 2A) can be percutaneously advanced into the vasculature of the patient and navigated within the patient's vasculature to the targeted vessel 180. Techniques such as x-ray fluoroscopy or ultrasonic imaging may be used to provide visualization of the introducer sheath and other atherectomy system components during placement. A guidewire (not shown in FIG. 2A) can then be inserted through a lumen of the introducer sheath and advanced to extend beyond the distal tip of the introducer sheath (and, optionally, through the area of the stenotic lesion 190). Next, the rotational atherectomy device 100 can be inserted over the guidewire (via the lumen 115) and advanced to the deployed position shown (optionally, the introduced sheath can be withdrawn before the rotational atherectomy device is advanced over the guidewire). In some implementations, a flush tube (e.g., refer to FIGS. 8 and 9) may surround a portion of the drive shaft 110 while the rotational atherectomy device 100 is so inserted over the guidewire.

In the deployed position as shown in the embodiment depicted in FIG. 2A, the eccentric abrasive element 140 is positioned near to the lesion 190 such that the eccentric abrasive element 140 can contact the lesion 190 when the drive shaft 110 is later rotated and advanced to remove the lesion 190. After the rotational atherectomy device 100 is placed in the deployed position, the guidewire is pulled back from within the lumen 115 of the drive shaft 110. In some implementations, the guidewire is withdrawn completely out of the lumen 115 of the drive shaft 110. In other implementations, the guidewire is withdrawn only partially (e.g., to a position that is proximal of the proximal stability element 120 and preferably proximal of the distal tip of the flush tube. That is, in some implementations a portion of the guidewire remains within the lumen of the drive shaft 110 during rotation of the drive shaft 110, but remains only in the portion that is not subject to the significant orbital path in the area of the abrasive element 140. After the guidewire is withdraw (fully or partially), the drive shaft 110 is then rotated (via the actuator located at the proximal end outside of the patient's body) at a high degree of rotation (e.g., 20,000-160,000 rpm) such that the eccentric abrasive element 140 revolves in an orbital path about an axis of rotation 103 and thereby contacts and removes portions of the lesion 190, even those portions of the lesion 190 that are spaced further from the axis of rotation 103 than the maximum diameter of the abrasive element 140.

Figure 2B:
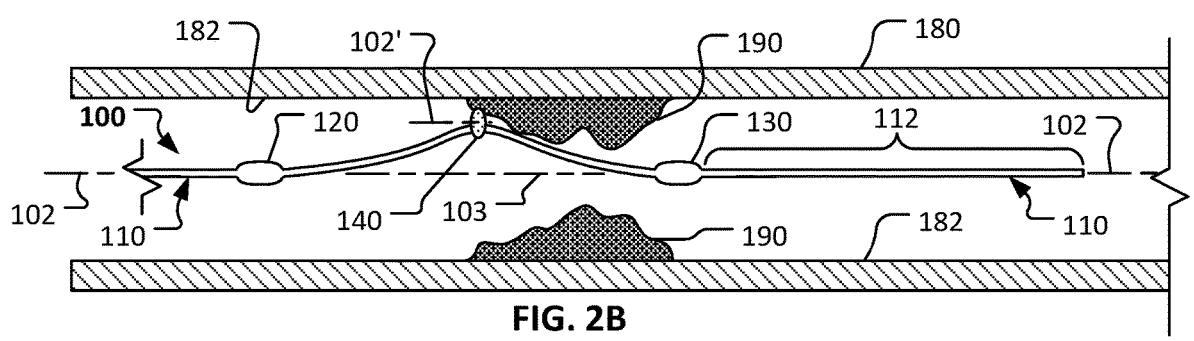
FIGS. 2B through 2D illustrate the rotational atherectomy device of FIG. 2A being rotated to provide an atherectomy treatment.
Figure 2C:
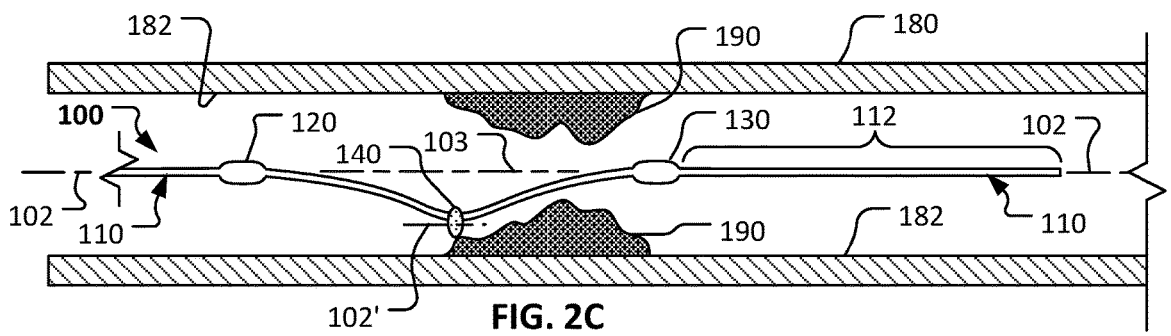
Figure 2D:
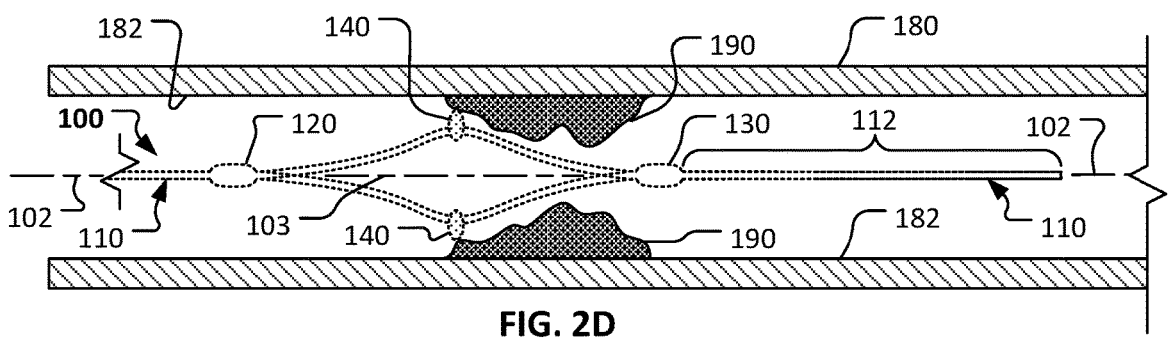

Referring now to FIGS. 2B through 2D, the rotational atherectomy device 100 is depicted during the high-speed rotation of the drive shaft 110. The centrifugal force acting on the eccentrically weighted abrasive element 140 causes the eccentric abrasive element 140 to orbit in an orbital path around the axis of rotation 103. In some implementations, the orbital path can be somewhat similar to the motion of a "jump rope." As shown in FIGS. 2B-2D, some portions of the drive shaft 102 (e.g., a portion that is proximal of the proximal stability element 120 and another portion that is distal of the distal stability element 130) can be aligned with the axis of rotation 103, but the particular portion of the drive shaft 110 adjacent to the abrasive element 140 is not aligned with the axis of rotation 103 (and instead orbits around the axis 103). In such circumstances, the longitudinal axis 102 of the drive shaft 110 in those particular portions (e.g., the shaft portion that is proximal of the proximal stability element 120 and the other shaft portion that is distal of the distal stability element 130) may be generally axially aligned with the axis of rotation 103, as shown in FIGS. 2B-D. It should be understood from the description herein that the term "generally axially aligned" is intended to account for the momentary variances that occur in the drive shaft position due to the high-speed rotation of the drive shaft, but that the longitudinal axis 102' (FIGS. 2B-2C) at the particular portion of the drive shaft 110 adjacent to the abrasive element 140 is not generally axially aligned with the axis of rotation 103 during the high speed rotation. In some implementations, as the eccentric abrasive element 140 rotates, the clinician operator slowly advances the atherectomy device 100 distally (an, optionally, reciprocates both distally and proximally) in the axial direction so that the abrasive surface of the eccentric abrasive element 140 scrapes against additional portions of the occluding lesion 190 to reduce the size of the occlusion, and to thereby improve the blood flow through the vessel 180.

During rotation of the atherectomy device 100, the proximal and distal stability elements 120 and 130, as well as the distal drive shaft extension portion 112, can be configured to advantageously achieve improved stability for the drive shaft 110 relative to the axis or rotation 103. For example, the device 100 can achieve a stable and predictable rotary motion profile in which the shaft portion that is proximal of the proximal stability element 120 and the other shaft portion that is distal of the distal stability element 130 remain generally aligned with the axis of rotation 103, even though the particular portion of the drive shaft 110 adjacent to the abrasive element 140 is not generally aligned with the axis of rotation 103 (and instead orbits around the axis 103). In this stability rotary motion profile, the eccentric abrasive element can follow a predictable orbital path (offset from an axis of rotation 103), yet other portions of the drive shaft 110 (especially the distal extension 112) can remain in a substantially stable axial alignment that greatly reduces the likelihood of uncontrolled whipping of the distal-most tip of the drive shaft 110 (which might cause unnecessary damage to the vessel wall 182). For example, such stability can be achieved by selecting some or all of the following design aspects of the rotational atherectomy device 100: (i) the mass of the proximal and distal stability elements 120 and 130, (ii) the length of the distal drive shaft extension portion 112 as a ratio to the distance between the proximal and distal stability elements 120 and 130 and the eccentric abrasive element 140, and (iii) the stiffness of the drive shaft 110 including any coating 116 on the drive shaft 110. In some embodiments, different coatings 116 (e.g., different materials and/or durometers) are used on different portions of the drive shaft 110 to enhance the in-operation stability of the rotational atherectomy device 100. In particular embodiments, multiple layers of coatings can be used on different portions of the drive shaft 110 to enhance the in-operation stability of the rotational atherectomy device 100.

As best seen in FIG. 2D, when rotating, the operative portion of the drive shaft 110 between the proximal and distal support elements 120 and 130 traces a generally bicone shape. By providing this predicable shape during high-speed rotation of the drive shaft 110, the shaft portion that is proximal of the proximal stability element 120 and the other shaft portion that is distal of the distal stability element 130 can remain both generally aligned with one another and can remain in a generally stable position within the vessel 180 (e.g., centrally aligned with the vessel 180). Also, when the device 100 provides this stable and predictable rotary motion profile, the orbital path of the abrasive element 140 is substantially greater than any orbital path of the proximal and distal stability elements 120 and 130 (if those elements 120 and 130 have any orbital path at all). As shown in the example in FIG. 2D, the orbital path diameter of the abrasive element 140 is substantially greater than the maximum diameter of the rotational path of each of the proximal and distal stability elements 120 and 130.

Referring now to FIGS. 3A though 3D, some embodiments of a rotational atherectomy device 300 can include proximal and distal stability elements 320 and 330 that are uncoated in this embodiment. The other aspects (e.g., materials, structure, construction, and alternatives) of the rotational atherectomy device 300 are similar to the rotational atherectomy device 100 described above.

In the depicted embodiment, a coating 316 surrounds at least some sections of filars 314 of drive shaft 310 (e.g., from the stability elements 320 and 330 to an eccentric abrasive element 340, and on a distal driveshaft extension portion 312). However, the coating 316 does not surround the outer diameters of the proximal and distal stability elements 320 and 330 in this embodiment. In some embodiments, one stability element 320 or 330 may be coated while the other stability element 320 or 330 remains uncoated.

Referring now to FIGS. 4A and 4B, some embodiments of a rotational atherectomy device 400 can include multiple proximal stability elements 420*a-b* and multiple distal stability elements 430*a-b*. For example, as shown in FIGS. 4A-4B, the atherectomy device 400 includes two proximal stability elements 420*a-b* and two distal stability elements 430*a-b*. The other aspects (e.g., materials, structure, construction, and alternatives) of the rotational atherectomy device 400 can be similar to the rotational atherectomy device 100 described above. In some embodiments, the inclusion of such multiple stability elements can enhance the stability and predictability of rotary motion profile of the abrasive element 440 and the drive shaft 410 along the distal portion of the rotational atherectomy device 400.

In the depicted embodiment, each of the stability elements 420*a-b* and 430*a-b* has a center of mass that is axially aligned with a longitudinal axis 402 of drive shaft 410. However, in alternative embodiments the center of mass of one or more of the stability elements 420*a-b* and/or 430*a-b* may be offset from the longitudinal axis 402. In the depicted embodiment, a distal drive shaft extension portion 412 extends distally from the distal-most stability element 430*b*. However, in alternative embodiments, the distal driveshaft extension portion 412 may be omitted. In the depicted embodiment, the outer diameters of the stability elements 420*a-b* and 430*a-b* are surrounded by a coating 416, which can be similar to the coating 116 described in connection with FIGS. 1A-D. However, in alternative embodiments one or more of the stability elements 420*a-b* and 430*a-b* may be uncoated.

In some embodiments, the stability elements 420*a* and 420*b* (and the same applies to the stability elements 430*a* and 430*b*) are spaced closely enough together such that the stability elements 420*a* and 420*b* perform much like a single stability element to stabilize the drive shaft 410. In alternative embodiments, the stability elements 420*a* and 420*b* (and the same applies to the stability elements 430*a* and 430*b*) are spaced apart from each other enough such that the stability elements 420*a* and 420*b* perform much like independent stability elements to stabilize the drive shaft 410.

Referring now to FIGS. 5A and 5B, some embodiments of a rotational atherectomy device 500 can include three proximal stability elements 520*a-c* and three distal stability elements 530*a-c*. The other aspects (e.g., materials, structure, construction, and alternatives) of the rotational atherectomy device 500 can be similar to the rotational atherectomy device 100 described above. In some embodiments, the inclusion of such multiple stability elements can enhance the stability and predictability of rotary motion profile of the abrasive element 540 and the drive shaft 510 along the distal portion of the rotational atherectomy device 500.

In the depicted embodiment, each of the stability elements 520*a-c* and 530*a-c* has a center of mass that is axially aligned with a longitudinal axis 502 of drive shaft 510. However, in alternative embodiments the center of mass of one or more of the stability elements 520*a-b-c* and 530*a-b-c* may be offset from the longitudinal axis 502. In the depicted embodiment, a distal driveshaft extension portion 512 extends distally from the distal-most stability element 530*c*. However, in alternative embodiments the distal drive shaft extension portion 512 may be omitted. In the depicted embodiment, the outer diameters of the stability elements 520*a-b-c* and 530*a-b-c* are uncoated. However, in alternative embodiments the outer diameters of one or more of the stability elements 520*a-b-c* and 530*a-b-c* may be surrounded by a coating 516, which can be similar to the coating 116 described in connection with FIGS. 1A-D.

Figure 6:
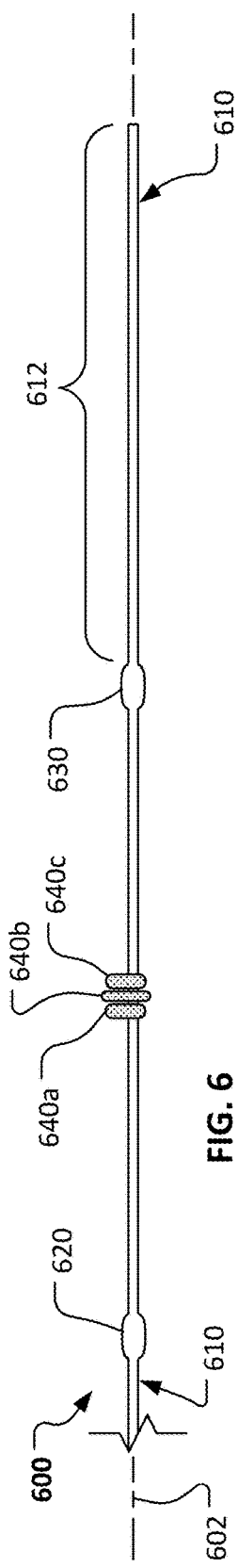
FIG. 6 is a side view of a distal portion of another rotational atherectomy device, in accordance with some embodiments.

Referring now to FIG. 6, some embodiments of a rotational atherectomy device 600 can include a segmented eccentric abrasive element that includes multiple side-by-side abrasive segments 640*a-c*. The other aspects (e.g., materials, structure, construction, and alternatives) of the rotational atherectomy device 600 are similar to the rotational atherectomy device 100 described above. In some embodiments, the inclusion of the segmented abrasive element 640*a-c* can enhance the flexibility of the portion of the drive shaft 610 within the segments 640*a-c*, thereby providing (in some circumstances) a greater orbital path diameter as compared to other embodiments having a single, elongate abrasive element. The segmentation of the abrasive element 640*a-c* can also provide for a wider abrasive element, thereby increasing the treatment efficiency (e.g., reducing the treatment time) of the rotational atherectomy device 600.

Figure 6A:
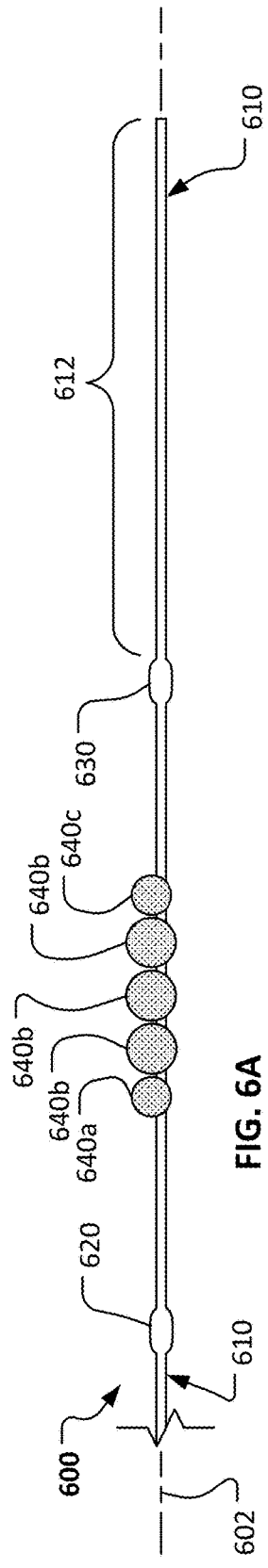
FIG. 6A is a side view of a distal portion of yet another rotational atherectomy device, in accordance with some embodiments.

In the depicted embodiment, the segmented eccentric abrasive element 640*a-c* includes three segments. In alternative embodiments, two, four, five, or more than five segments can be included (refer, for example, to FIG. 6A depicting five). In the depicted embodiment, all three segments 640*a-c* have centers of mass that are offset from a longitudinal axis 602 of a drive shaft 610. In alternative embodiments, one or more of the segments may have a center of mass that is aligned with the longitudinal axis 602 while the other segment(s) is eccentric and thus not aligned with the longitudinal axis 602. In the depicted embodiment, all three segments 640*a-c* are shaped as ellipsoids. In alternative embodiments, one or more of the segments may have a different shape such as, but not limited to, spherical, (refer, for example, to FIG. 6A), cylindrical, conical, frustro conical, polyhedral, and the like. In the depicted embodiment, (FIG. 6A), the outer diameters of the two outer abrasive elements 640*a* and 640*c* are smaller than the central abrasive element 640*b* (refer, for example, to FIG. 6A). Together, the segmented eccentric abrasive element 640*a-b-c* therefore has a tapered outer profile. In alternative embodiments, all segments may have essentially the same outer diameter, or may define a different outer profile shape.

Figure 7:
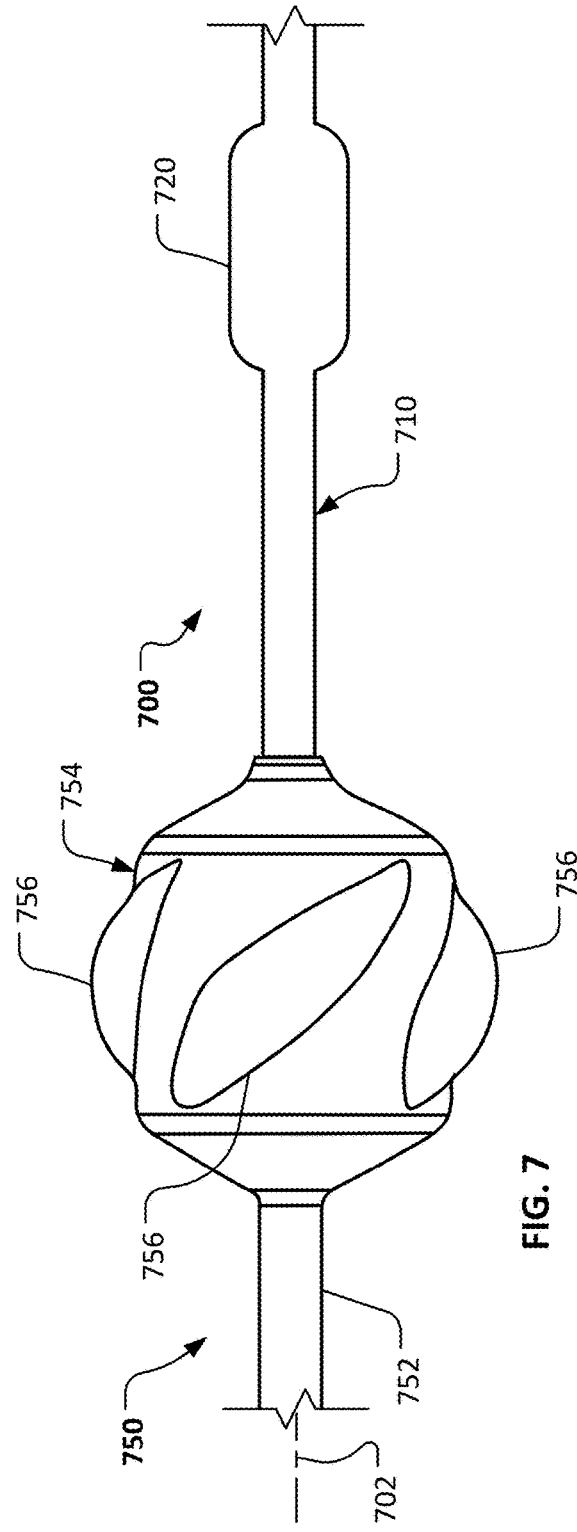
FIG. 7 is a side view of a distal portion of a rotational atherectomy system, including a flush tube with a proximal stabilization balloon, in accordance with some embodiments.

Referring now to FIG. 7, as previously described herein, some embodiments of a rotational atherectomy system include a rotational atherectomy device 700 and a flush tube 750. The rotational atherectomy device 700 can be configured as any of the above-described atherectomy devices 100, 300, 400, 500, and 600. In use, a portion of a drive shaft 710 of the rotational atherectomy device 700 can be slidably positioned within a lumen of the flush tube 750. As such, while the drive shaft 710 is rotating at a high speed (e.g., 20,000 to 180,000 rpm), the flush tube 750 can remain stationary relative to the vessel wall. In these circumstances, the flush tube 750 can further enhance to the stability of the portion of the drive shaft 710 that is proximal to the abrasive element (not shown in FIG. 7, refer to FIG. 8) and improve the predictability of the rotary motion profile of the abrasive element. In some embodiments, the flush tube also increases the column strength (and therefore the ability to be pushed) of the drive shaft and flush tube system 710 and 750 during the system's advancement over the guidewire within the vasculature of the patient.

In this embodiment, the flush tube 750 includes a multi-lumen shaft 752 and a stabilization balloon 754, which can be inflated after deployment into the targeted vessel. The stabilization balloon 754 is attached to a distal end portion of the multi-lumen shaft 752 and is in fluid communication with an inflation lumen of the multi-lumen shaft 752. The inflation lumen of the multi-lumen shaft 752 can be used to convey an inflation fluid (e.g., saline) to the stabilization balloon 754. When inflation fluid is supplied to the stabilization balloon 754, the stabilization balloon 754 can expand to the configuration shown. Conversely, when inflation fluid is not supplied to the stabilization balloon 754, the stabilization balloon 754 contracts to a configuration that is smaller in size than the expanded configuration shown.

In addition to the inflation lumen, the multi-lumen shaft 752 includes a longitudinal drive shaft lumen in which a portion of the drive shaft 710 can be slidably positioned. A physical clearance exists between the outer diameter of the drive shaft 710 and the inner diameter of the drive shaft lumen. The clearance allows the drive shaft 710 to freely rotate while the flush tube 750 is stationary relative to the vessel. In some embodiments, the clearance is in a range of about 0.05 mm to about 0.15 mm, or about 0.13 mm to about 0.23 mm, or about 0.20 mm to about 0.30 mm, or about 0.28 mm to about 0.38 mm, or about 0.35 mm to about 0.46 mm, or more than about 0.46 mm. In addition to allowing the drive shaft 710 to rotate while the flush tube 750 is stationary, the clearance therebetween can be used to covey a flush fluid (e.g., saline). The flush fluid prevents blood from the vessel being treated from backing up into the clearance space. In addition, in some embodiments the flush fluid can provide cooling and lubrication to the surface friction between the drive shaft 710 and the drive shaft lumen of the flush tube 750 as the drive shaft 710 is rotating.

Still referring to FIG. 7, in some embodiments, the stabilization balloon 754 can include one or more ribs 756. As will be described further below, the ribs 756 facilitate the flow of blood past the stabilization balloon 754 even while the stabilization balloon 754 is in an expanded configuration and in contact with an inner wall of the targeted vessel. This feature for facilitating blood flow is advantageous in that blood flow is not cut off during an atherectomy procedure. While the depicted embodiment of stabilization balloon 754 includes the ribs 756, in alternative embodiments other types of features for facilitating blood flow through or around a stabilization balloon can be included. For example, in some embodiments features such as, but not limited to, through-holes or lumens, grooves, and the like, can be included to facilitate blood flow through or around a stabilization balloon.

Referring to FIG. 8, the rotational atherectomy device 700 in conjunction with the flush tube 750 can be used to provide an atherectomy treatment to a stenotic lesion 890 within a vessel 880. The vessel 880 and lesion 890 are shown in longitudinal cross-sectional views to enable visualization of the rotational atherectomy device 700 and the flush tube 750. In some implementations, the flush tube 750 can further enhance to the stability of the portion of the drive shaft 710 that is proximal to the abrasive element 740 and improve the predictability of the rotary motion profile of the abrasive element 740.

During rotation of the drive shaft 710 about its axis 702, the stabilization balloon 756 is in an expanded configuration as shown. As such, the ribs 756 make contact with the inner wall of the vessel 880 to maintain the position of the balloon 756 relative to the vessel 880 while also permitting continued blood flow pass the balloon 756. The drive shaft 710 can then be rotated to cause the eccentric abrasive element 740 to orbit around the axis of rotation 703 of the atherectomy device 700 to ablate the lesion 890. Similar to previously described embodiments, the device 700 can achieve a stable and predictable rotary motion profile in which the shaft portion that is proximal of the proximal stability element 720 and the other shaft portion that is distal of the distal stability element 730 remain generally aligned with the axis of rotation 703, even though the particular portion of the drive shaft 710 adjacent to the abrasive element 740 is not generally aligned with the axis of rotation 703 (and instead orbits around the axis 703). The flush tube 750 remains substantially stationary as the drive shaft 710 is rotated. The contact between the ribs 756 and the inner wall of the vessel 880 help the stabilization balloon 754 to further stabilize the atherectomy device 700 during rotation and to also centrally position the shaft portion that is proximal of the proximal stability element 720 within the targeted vessel 880. During the atherectomy procedure, on-going blood flow through the vessel 880 is facilitated by the channel spaces defined between the ribs 756 of the stabilization balloon 754.

Referring to FIG. 9, another embodiment of a rotational atherectomy can include an alternative rotational atherectomy device 900 and the previously described flush tube 750, which can be used together to provide an atherectomy treatment to a stenotic lesion 990 within a targeted vessel 980. In this embodiment, the rotational atherectomy device 900 includes a distal stability element 930, but does not include a corresponding proximal stability element. Rather, the stabilization balloon 754 of the flush tube 750 provides the function of stabilizing the portion of the drive shaft 910 that is proximal of the abrasive element 940 during high-speed rotation of the drive shaft 910. Thus, the stabilization balloon 754 and the distal stability element can work in tandem to provide a stable and predictable rotary motion profile in which the shaft portion that is proximal of the abrasive element 940 (and immediately adjacent to the balloon 754) and the other shaft portion that is distal of the distal stability element 930 remain generally aligned with the axis of rotation 903, even though the particular portion of the drive shaft 910 adjacent to the abrasive element 940 is not generally aligned with the axis of rotation 903 (and instead orbits around the axis 903).

A number of embodiments of the invention have been described. Nevertheless, it will be understood that various modifications may be made without departing from the spirit and scope of the invention. For example, design features of the embodiments described herein can be combined with other design features of other embodiments described herein. Accordingly, other embodiments are within the scope of the following claims.

What is claimed is:

1. A system for performing rotational atherectomy to remove stenotic lesion material from a blood vessel of a patient, the system comprising:
an elongate tube defining a lumen; and
a rotational atherectomy device comprising:
an elongate flexible drive shaft comprising helically wound metallic filars that form a coil having an outer diameter, the drive shaft defining a longitudinal axis;
an array of at least three spherical eccentric abrasive elements being fixed to the drive shaft such that a center of mass of each abrasive element is offset from the longitudinal axis, each abrasive element being spaced apart from an adjacent abrasive element by an element spacing distance; and
a metallic stability element having a cylindrical shape defining an inner diameter, the metallic stability element being fixed along the inner diameter to the helically wound metallic filars of the drive shaft, the metallic stability element having a center of mass aligned with the longitudinal axis;
wherein the drive shaft, the spherical eccentric abrasive elements, and the metallic stability element rotate together about the longitudinal axis,
wherein the stability element being distally spaced apart from a distal-most abrasive element of the spherical eccentric abrasive elements by a distal separation distance, and
wherein the distal separation distance being greater than the element spacing distance.

2. The system of claim 1, wherein the at least three spherical eccentric abrasive elements are positioned adjacent to one another along the coil.

3. The system of claim 1, further comprising a guidewire configured to be slidably disposed within a fluid-impermeable lumen of the drive shaft.

4. The system of claim 1, wherein the drive shaft has a central lumen extending along the longitudinal axis that is configured to receive a guidewire, and wherein the coil formed by the helically wound metallic filars has a constant outer coil diameter.

5. The system of claim 1, wherein the coil of the drive shaft comprises a torque-transmitting coil and wherein the metallic stability element comprises a hollow metallic cylinder with the inner diameter that is fixed to an outer diameter of the torque-transmitting coil.

6. A system for performing rotational atherectomy to remove stenotic lesion material from a blood vessel of a patient, the system comprising:
an elongate tube defining a lumen; and
a rotational atherectomy device comprising:
an elongate flexible drive shaft comprising helically wound metallic filars that form a coil having an outer diameter, the drive shaft defining a longitudinal axis;
an array of at least three spherical eccentric abrasive elements being fixed to the drive shaft such that a center of mass of each abrasive element is offset from the longitudinal axis, each abrasive elements being spaced apart from an adjacent abrasive element by an element spacing distance; and
a metallic stability element having a cylindrical shape defining an inner diameter, the metallic stability element being fixed along the inner diameter to the helically wound metallic filars of the drive shaft, the metallic stability element having a center of mass aligned with the longitudinal axis;
wherein the drive shaft, the spherical eccentric abrasive elements, and the metallic stability element rotate together about the longitudinal axis,
the system further comprising a second stability element fixed to the drive shaft.

7. The system of claim 6, wherein the metallic stability element being distally spaced apart from a distal-most abrasive element of the spherical eccentric abrasive elements by a distal separation distance.

8. The system of claim 6, wherein the second stability element is located proximally of the abrasive elements.

9. The system of claim 6, further comprising a guidewire configured to be slidably disposed within a fluid-impermeable lumen of the drive shaft.

10. The system of claim 6, wherein the spherical eccentric abrasive elements are positioned adjacent to one another along the drive shaft.

11. The system of claim 6, wherein the abrasive elements comprises five spherical eccentric abrasive elements positioned along the drive shaft.

12. The system of claim 6, wherein the drive shaft has a central lumen extending along the longitudinal axis that is configured to receive a guidewire, and wherein the coil formed by the helically wound metallic filars has a constant outer coil diameter.

13. The system of claim 6, wherein the coil of the drive shaft comprises a torque-transmitting coil and wherein the metallic stability element comprises a hollow metallic cylinder with the inner diameter that is fixed to an outer diameter of the torque-transmitting coil.

14. The system of claim 13, wherein the hollow metallic cylinder has an axial length that is greater than a maximum exterior diameter of the hollow metallic cylinder.

15. A system for performing rotational atherectomy to remove stenotic lesion material from a blood vessel of a patient, the system comprising:
  an elongate tube defining a lumen; and
  a rotational atherectomy device comprising:
    an elongate flexible drive shaft comprising helically wound metallic filars that form a coil having an outer diameter, the drive shaft defining a longitudinal axis;
    an array of five spherical eccentric abrasive elements being fixed to the drive shaft such that a center of mass of each abrasive element is offset from the longitudinal axis,
    each abrasive element being spaced apart from an adjacent abrasive element by an element spacing distance; and
    a metallic stability element having a cylindrical shape defining an inner diameter, the metallic stability element being fixed along the inner diameter to the helically wound metallic filars of the drive shaft, the metallic stability element having a center of mass aligned with the longitudinal axis;
  wherein the drive shaft, the spherical eccentric abrasive elements, and the metallic stability element rotate together about the longitudinal axis, and
  wherein the array comprises outer spherical eccentric abrasive elements and at least one inner spherical eccentric abrasive element, wherein an outer diameter of each of the outer spherical eccentric abrasive element is smaller than an outer diameter of the at least one inner spherical eccentric abrasive element.

16. The system of claim 15, wherein the drive shaft has a central lumen extending along the longitudinal axis that is configured to receive a guidewire, and wherein the coil formed by the helically wound metallic filars has a constant outer coil diameter.

17. The system of claim 15, further comprising a guidewire configured to be slidably disposed within a fluid-impermeable lumen of the drive shaft.

18. The system of claim 15, wherein the spherical eccentric abrasive elements are positioned adjacent to one another along the drive shaft.

19. The system of claim 15, wherein the metallic stability element comprises a hollow metallic cylinder with an exterior cylindrical surface.

20. The system of claim 15, wherein the coil of the drive shaft comprises a torque-transmitting coil and wherein the metallic stability element comprises a hollow metallic cylinder with the inner diameter fixed to an outer diameter of the torque-transmitting coil.

21. The system of claim 20, wherein the hollow metallic cylinder has an axial length that is greater than a maximum exterior diameter of the hollow metallic cylinder.

22. A system for performing rotational atherectomy to remove stenotic lesion material from a blood vessel of a patient, the system comprising:
  an elongate tube defining a lumen; and
  a rotational atherectomy device comprising:
    an elongate flexible drive shaft comprising helically wound metallic filars that form a coil having an outer diameter, the drive shaft defining a longitudinal axis;
    an array of at least three spherical eccentric abrasive elements being fixed to the drive shaft such that a center of mass of each abrasive element is offset from the longitudinal axis, each abrasive elements being spaced apart from an adjacent abrasive element by an element spacing distance; and
    a metallic stability element having a cylindrical shape defining an inner diameter, the metallic stability element being fixed along the inner diameter to the helically wound metallic filars of the drive shaft, the metallic stability element having a center of mass aligned with the longitudinal axis;
  wherein the drive shaft, the spherical eccentric abrasive elements, and the metallic stability element rotate together about the longitudinal axis, and
  wherein each spherical eccentric abrasive element of the at least three spherical eccentric abrasive elements has an abrasive outer surface, and wherein a middle spherical eccentric abrasive element of the at least three spherical eccentric abrasive elements has a larger outer diameter than a proximal spherical eccentric abrasive element of the at least three spherical eccentric abrasive elements and a larger outer diameter than a distal spherical eccentric abrasive element of the at least three spherical abrasive elements.

23. The system of claim 22, wherein the metallic stability element comprises a hollow metallic cylinder with an exterior cylindrical surface.

24. The system of claim 22, wherein the system includes a means for stabilizing a portion of the drive shaft that is proximal of the abrasive elements.

25. The system of claim 22, wherein the drive shaft has a central lumen extending along the longitudinal axis that is configured to receive a guidewire, and wherein the coil formed by the helically wound metallic filars has a constant outer coil diameter.

26. The system of claim 22, wherein the coil of the drive shaft comprises a torque-transmitting coil and wherein the metallic stability element comprises a hollow metallic cylinder with the inner diameter that is fixed to an outer diameter of the torque-transmitting coil.

27. The system of claim 22, wherein the spherical eccentric abrasive elements are positioned adjacent to one another along the drive shaft.

28. The system of claim 22, wherein the system includes an inflatable balloon member attached to and surrounding an outer diameter of a distal end portion of the elongate tube, the balloon member is in fluid communication with the lumen, and the balloon member is configured to contact a blood vessel wall when the balloon member is in an inflated configuration.

29. The system of claim 28, wherein an outer surface of the balloon member defines channel spaces configured to allow blood flow past the balloon member when the balloon member is in the inflated configuration and in contact with the blood vessel wall.

30. The system of claim 22, wherein the drive shaft has an outer diameter covered by a flexible polymer coating.

31. The system of claim 30, wherein the flexible polymer coating comprises a fluid-impermeable material that provides a fluid-impermeable lumen along the drive shaft.

* * * * *